(12) United States Patent
Peng et al.

(10) Patent No.: US 9,456,871 B2
(45) Date of Patent: *Oct. 4, 2016

(54) SIDE-FIRING FIBER DELIVERY DEVICE WITH ACTIVE COOLING CAP

(71) Applicant: Boston Scientific Scimed, Inc., Maple Grove, MN (US)

(72) Inventors: Yihlih Peng, Fremont, CA (US); Gerald M. Mitchell, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,945

(22) Filed: Aug. 28, 2014

(65) Prior Publication Data

US 2015/0011985 A1     Jan. 8, 2015

Related U.S. Application Data

(63) Continuation of application No. 12/185,592, filed on Aug. 4, 2008, now Pat. No. 8,858,542.

(60) Provisional application No. 60/953,721, filed on Aug. 3, 2007.

(51) Int. Cl.
*A61B 18/20*     (2006.01)
*A61B 18/22*     (2006.01)
(Continued)

(52) U.S. Cl.
CPC .............. *A61B 18/22* (2013.01); *G02B 6/241* (2013.01); *G02B 6/443* (2013.01); *G02B 6/4415* (2013.01);
(Continued)

(58) Field of Classification Search
CPC .......... A61B 18/24; A61B 2018/2272; A61B 18/18; A61B 1/015; A61B 18/22; A61B 2018/0029; A61B 2018/00023; A61B 2018/2205; G02B 6/241; G02B 6/4415
See application file for complete search history.

(56) References Cited

U.S. PATENT DOCUMENTS 4,325,006 A   4/1982 Morton
4,572,609 A   2/1986 Sakuragi et al.
(Continued)

FOREIGN PATENT DOCUMENTS

CN   1617039 A    5/2005
EP   0407229 A3   1/1991
(Continued)

OTHER PUBLICATIONS

Gosnell, T.R., "Laser cooling of a solid by 65 K starting from room temperature" Optics Letters vol. 24, No. 15 Aug. 1999 1041-43.
(Continued)

*Primary Examiner* — Gary Jackson
*Assistant Examiner* — Scott T Luan
(74) *Attorney, Agent, or Firm* — Bookoff McAndrews, PLLC

(57) ABSTRACT

An optical fiber includes an internal fiber, an end surface, a first cap member and a second cap member. The internal fiber terminates at a fiber tip. The end surface transmits laser energy delivered through the internal fiber. The first cap member extends over the end surface and includes a first end on a first side of the end surface and a second end on a second side of the end surface. The second cap member extends over the first cap member and includes a first end on the first side of the end surface and a second end on the second side of the end surface, the second end of the second cap member is attached to the second end of the first cap member.

20 Claims, 5 Drawing Sheets

(51) Int. Cl.
  *G02B 6/24* (2006.01)
  *G02B 6/44* (2006.01)
  *A61B 18/00* (2006.01)

(52) U.S. Cl.
  CPC .......... *A61B 2018/00023* (2013.01); *A61B 2018/00029* (2013.01); *A61B 2018/2205* (2013.01); *A61B 2018/2272* (2013.01)

(56) References Cited

U.S. PATENT DOCUMENTS

| | | | |
|---|---|---|---|
| 4,694,828 | A | 9/1987 | Eichenbaum |
| 4,707,073 | A | 11/1987 | Kocher |
| 4,806,289 | A | 2/1989 | Laursen et al. |
| 4,832,024 | A * | 5/1989 | Boussignac et al. ............ 606/7 |
| 4,945,457 | A | 7/1990 | Yazdani et al. |
| 5,064,271 | A | 11/1991 | Kern et al. |
| 5,076,653 | A | 12/1991 | Kayashima et al. |
| 5,203,780 | A | 4/1993 | Liebler |
| 5,222,174 | A | 6/1993 | Miles |
| 5,320,617 | A | 6/1994 | Leech |
| 5,409,483 | A | 4/1995 | Campbell et al. |
| 5,416,878 | A | 5/1995 | Bruce |
| 5,437,660 | A | 8/1995 | Johnson et al. |
| 5,471,553 | A | 11/1995 | Teshima |
| 5,496,307 | A * | 3/1996 | Daikuzono .................... 606/15 |
| 5,571,151 | A | 11/1996 | Gregory |
| 5,593,404 | A | 1/1997 | Costello et al. |
| 5,737,473 | A | 4/1998 | Nath |
| 5,760,364 | A | 6/1998 | Marlier et al. |
| 5,762,493 | A | 6/1998 | Rechmann |
| 5,785,704 | A | 7/1998 | Bille et al. |
| 5,836,941 | A | 11/1998 | Yoshihara et al. |
| 5,925,012 | A | 7/1999 | Murphy-Chutorian et al. |
| 5,999,678 | A | 12/1999 | Murphy-Chutorian et al. |
| 6,229,939 | B1 | 5/2001 | Komine |
| 6,299,599 | B1 | 10/2001 | Pham et al. |
| 6,343,174 | B1 | 1/2002 | Neuberger |
| 6,554,824 | B2 | 4/2003 | Davenport et al. |
| 6,574,401 | B2 | 6/2003 | Neuberger |
| 6,802,838 | B2 | 10/2004 | Loeb et al. |
| 6,888,097 | B2 | 5/2005 | Batarseh |
| 6,981,804 | B2 | 1/2006 | Jian |
| 6,986,764 | B2 | 1/2006 | Davenport et al. |
| 7,331,954 | B2 | 2/2008 | Temelkuran et al. |
| 7,457,502 | B2 | 11/2008 | Davis |
| 7,463,801 | B2 | 12/2008 | Brekke et al. |
| 8,858,542 | B2 | 10/2014 | Peng et al. |
| 2003/0199860 | A1 * | 10/2003 | Loeb et al. ..................... 606/17 |
| 2006/0224148 | A1 | 10/2006 | Cho et al. |
| 2007/0219544 | A1 | 9/2007 | Gowda et al. |
| 2007/0270788 | A1 * | 11/2007 | Nahen et al. ................... 606/15 |
| 2008/0195085 | A1 * | 8/2008 | Loeb ................................ 606/3 |

FOREIGN PATENT DOCUMENTS

| | | |
|---|---|---|
| EP | 00610991 A2 | 8/1994 |
| EP | 0561903 B1 | 7/1995 |
| EP | 01992301 A1 | 11/2008 |
| JP | 07080086 A2 | 3/1995 |
| JP | 28036025 A2 | 2/2008 |
| WO | 2006107522 A2 | 10/2006 |

OTHER PUBLICATIONS

Hashimoto, D., et al., "Cooling an optical fiber to 4.5 K by indirect thermal contact with a liquid-helium . . . " Rev. Sci. Instr. 79, 093102 (2008) 5 pp.

Maclaurin, P. et al., "Quantitative in Situ Monitoring of an Elevated Temperature Reaction Using a Water-Cooled Mid-Infrared Fiber-Optic Probe" Anal. Chem. 1996, 68, 116-1123.

Tokita, S. et al., "Liquid-cooled 24 W mid-infrared Er:ZBLAN fiber laser", Optics Letters vol. 34, No. 20 Oct. 2009, 3062-4.

Vaskopulous., T et al., "Cooling of optical fiber in aiding and opposing forced gas flow".

Office Action from related U.S. Appl. No. 12/185,592, mailed Jun. 6, 2012.

Final Office Action from related U.S. Appl. No. 12/185,592, mailed Oct. 11, 2012.

Office Action from related U.S. Appl. No. 12/185,592, mailed Nov. 20, 2013.

Final Office Action from related U.S. Appl. No. 12/185,592, mailed Apr. 28, 2014.

\* cited by examiner

SIDE-FIRING FIBER DELIVERY DEVICE WITH ACTIVE COOLING CAP

PRIORITY CLAIM

The present application is a continuation of U.S. patent application Ser. No. 12/185,592, filed Aug. 4, 2008 and issued Oct. 14, 2014 as U.S. Pat. No. 8,858,542, which is based on and claims the benefit of U.S. provisional patent application Ser. No. 60/953,721, filed Aug. 3, 2007. The above-referenced applications are hereby incorporated by reference in their entirety.

FIELD OF THE INVENTION

This invention relates to the field of medical lasers utilizing optical fibers. More specifically, the present invention relates to a side-firing optical fiber utilizing internal and external cooling streams to prevent premature failure at a fiber tip.

BACKGROUND OF THE INVENTION

Medical lasers have been used in treatment procedures involving various practice areas, including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy, and often the area to which the laser energy is to be delivered is located deep within the body; for example, at the prostate or at the fallopian tubes. Due to the location of the target tissue deep within the body, the medical procedure requires that the optical fiber be flexible and maneuverable. Various light sources can be used with optical fiber devices dependent upon the requirements for the light source; for example, pulsed lasers, diode lasers and neodymium lasers can be used as light sources. Representative lasers used in medical treatment procedures include Ho:YAG lasers and Nd:YAG lasers.

In medical procedures utilizing laser energy, the laser is coupled to an optical fiber adapted to direct laser radiation from the laser, through the fiber and to the treatment area. Typically, a surgical probe is utilized in the treatment of body tissue with laser energy. The surgical probe generally includes an optical fiber coupled to a laser source, and the probe tip is positioned on the optical fiber opposite the laser source, such that the tip of the probe can be positioned adjacent to the targeted tissue. Laser energy is directed out of the probe tip of the optical fiber onto desired portions of the targeted tissue.

Depending upon the operational conditions during laser treatment, a cap on the surgical probe can overheat. Overheating of the cap can lead to failure of the optical fiber. If the optical fiber fails, the laser system fails. Overheating of the cap can cause the cap to burn, detach, or even shatter during treatment inside the patient, which can lead to injury to the patient.

SUMMARY OF THE INVENTION

Some embodiments of the invention are directed to optical fibers and medical laser systems that may be used to deliver laser energy for performing a medical procedure. In some embodiments, an optical fiber includes an internal fiber, an end surface, a first cap member and a second cap member. The internal fiber terminates at a fiber tip. The end surface transmits laser energy delivered through the internal fiber. The first cap member extends over the end surface and includes a first end on a first side of the end surface and a second end on a second side of the end surface. The second cap member extends over the first cap member and includes a first end on the first side of the end surface and a second end on the second side of the end surface, the second end of the second cap member is attached to the second end of the first cap member.

In some embodiments, an optical fiber includes an internal fiber that terminates at a fiber tip. A reflective surface reflects laser energy transmitted through the internal fiber. An inner cap member extends over the reflective surface. An outer cap member extends over the inner cap member and includes an exterior surface having a side-firing port through which laser energy transmitted through the internal fiber and reflected by the reflective surface is discharged.

In some embodiments, an optical fiber includes an internal fiber that terminates at a fiber tip and A reflective surface reflects laser energy transmitted through the internal fiber. The optical fiber also includes a tip cap assembly comprising an inner cap member, an outer cap member, and a cap irrigation channel. The inner cap member extends over the reflective surface and includes a proximal end on a proximal side of the reflective surface and a distal end on a distal side of the reflective surface. The outer cap member extends over the inner cap member and includes (i) a distal end on the distal side of the reflective surface, the distal end of the outer cap member being attached to the distal end of the inner cap member, and (ii) an exterior surface having a port through which laser energy transmitted through the internal fiber and reflected by the reflective surface is discharged. The cap irrigation channel is between the inner cap member and the outer cap member.

Some embodiments of the medical laser system include a laser unit for generating laser treatment energy, and an optical fiber attached to the laser unit for delivering the laser treatment energy to a treatment location. In some embodiments, the optical fiber includes an internal fiber terminating at a fiber tip, a reflective surface that reflects laser energy transmitted through the internal fiber, and a tip cap assembly. In some embodiments, the tip cap assembly includes an inner cap member, an outer cap member and a cap irrigation channel between the inner cap member and the outer cap member. The inner cap member extends over the reflective surface. The outer cap member extends over the inner cap member and includes an exterior surface having a side-firing port through which laser energy transmitted through the internal fiber and reflected by the reflective surface is discharged.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention, will be more completely understood and appreciated by referring to the following more detailed description of the presently preferred exemplary embodiments of the invention in conjunction with the accompanying drawings of which.

Figure 1:
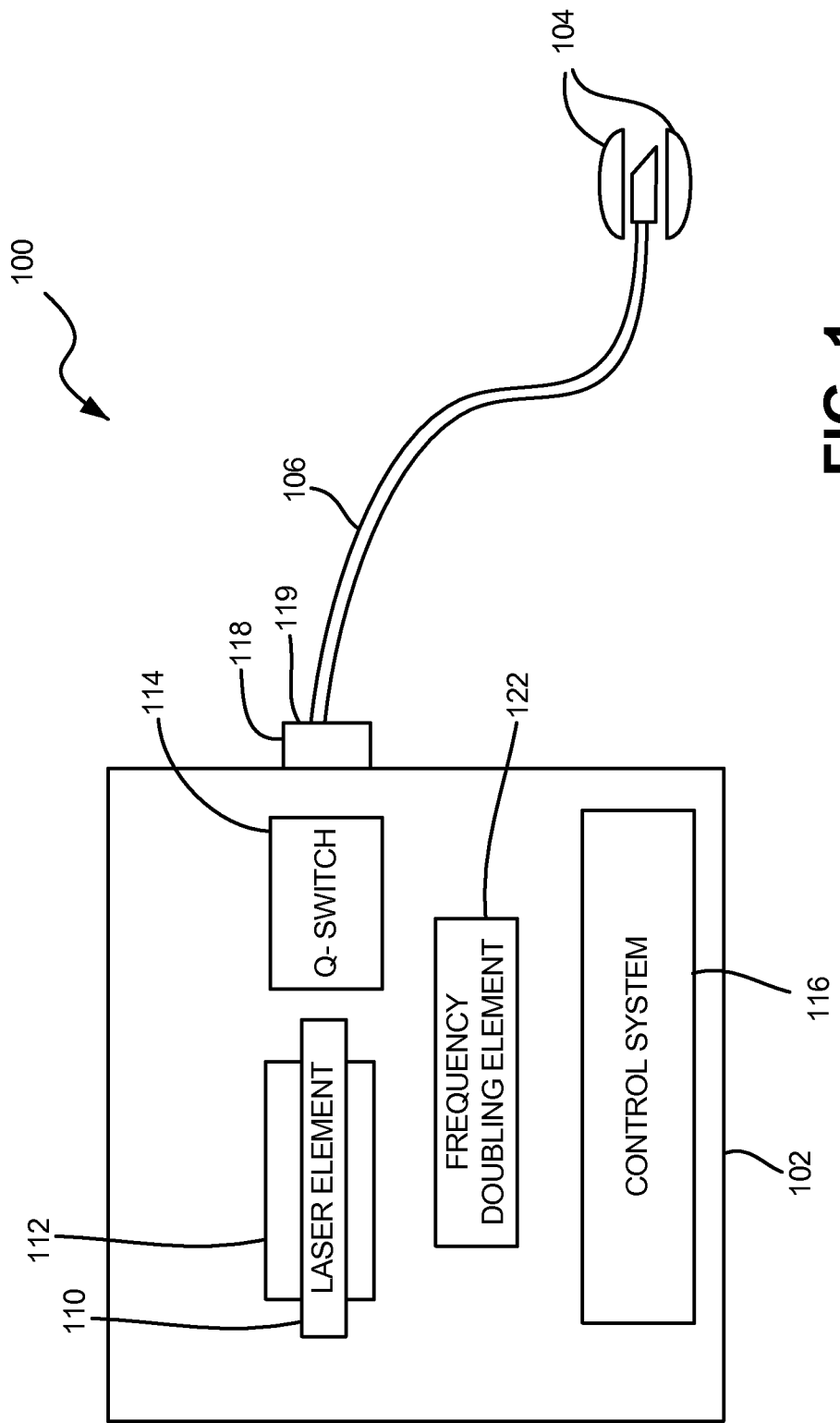
FIG. 1 is a block diagram illustration of a laser system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

The present invention comprises an optical fiber for use with a medical laser system that utilizes internal and external cooling streams and related methods of monitoring an optical fiber to determine if an optical fiber cap on the optical fiber is in imminent danger of cap failure. The laser system includes a photodetector for converting returned light from the optical fiber cap to an electronic signal for comparison to a trigger threshold value known to be indicative of imminent fiber cap failure. The returned light can be the main laser treatment wavelength, an auxiliary wavelength, such as an aiming beam, or infrared wavelengths generated by a temperature of the optical fiber cap. In the event the electronic signal reaches the trigger threshold value, the laser system can be temporarily shut-off or the power output can be reduced. In one preferred embodiment, the present invention can be utilized as part of a Greenlight HPS system manufactured by American Medical Systems of Minnetonka, Minn. and as described in U.S. Pat. Nos. 6,554,824 and 6,986,764, which are herein incorporated by reference.

Referring to FIG. 1, there is depicted a block diagram showing an exemplary laser system 100, which may be employed for implementing the present invention. Laser system 100 includes a solid-state laser unit 102, which is used to generate laser light for delivery through optical fiber 106 to target tissue 104. Laser unit 102 is capable of being operated in a pulsed mode or continuous wave.

Laser unit 102 more specifically comprises a laser element assembly 110, pump source 112, and frequency doubling crystal 122. In the preferred embodiment, laser element assembly 110 outputs 1064 nm of light, which is focused into frequency doubling crystal 122 to create 532 nm of light. According to one implementation, laser element assembly 110 may be a neodymium doped YAG (Nd:YAG) crystal, which emits light having a wavelength of 1064 nm (infrared light) when excited by pump source 112. Laser element assembly 110 may, alternatively, be fabricated from any suitable material, wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element assembly 110 is positioned proximal to pump source 112, and may be arranged in parallel relation therewith, although other geometries and configurations may be employed.

Pump source 112 may be any device or apparatus operable to excite laser element assembly 110. Non-limiting examples of devices which may be used as pump source 112 include: arc lamps, flashlamps, and laser diodes.

A Q-switch 114 disposed within laser unit 102 may be operated in a repetitive mode to cause a train of micropulses to be generated by laser unit 102. Typically the micropulses are less than 1 microsecond in duration separated by about 40 microseconds, creating a quasi-continuous wave train. Q-switch 114 is preferably of the acousto-optic type, but may, alternatively, comprise a mechanical device such as a rotating prism or aperture, an electro-optical device, or a saturable absorber.

Laser unit 102 is provided with a control system 116 for controlling and operating laser unit 102. Control system 116 will typically include a control processor which receives input from user controls (including but not limited to a beam on/off control, a beam power control, and a pulse duration control), and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn, controlling the pulse duration of the output beam. Laser unit 102 further includes an output port 118 couplable to a proximal end 119 of optical fiber 106. Output port 118 directs the light generated by laser unit 102 into optical fiber 106 for delivery to tissue 104.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm of light. The frequency doubled, shorter wavelength light is better absorbed by the hemoglobin and char tissue, and promotes more efficient tissue ablation.

Figure 2:
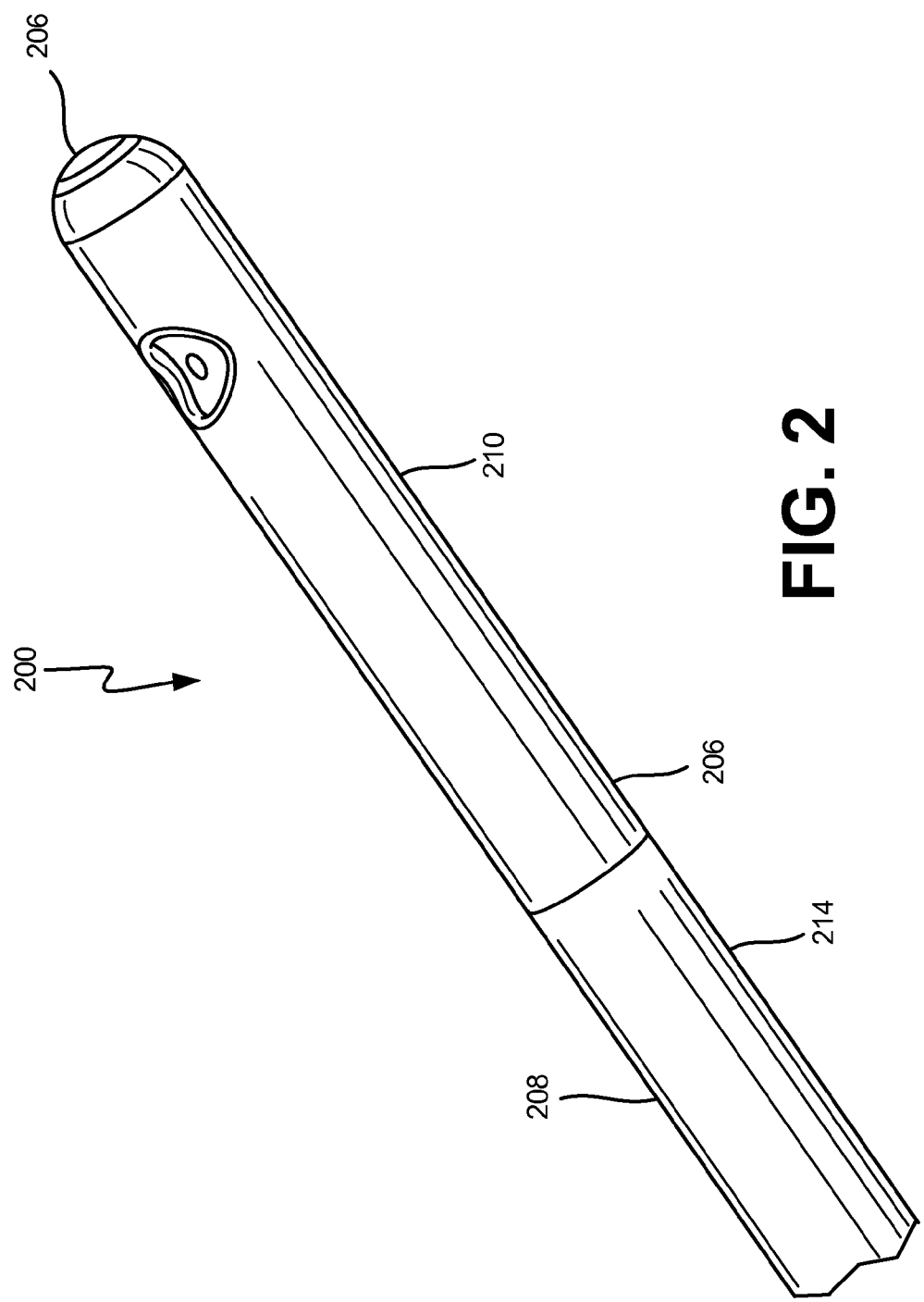
FIG. 2 is a perspective end view of an optical fiber according to an embodiment of the present invention.
Figure 3:
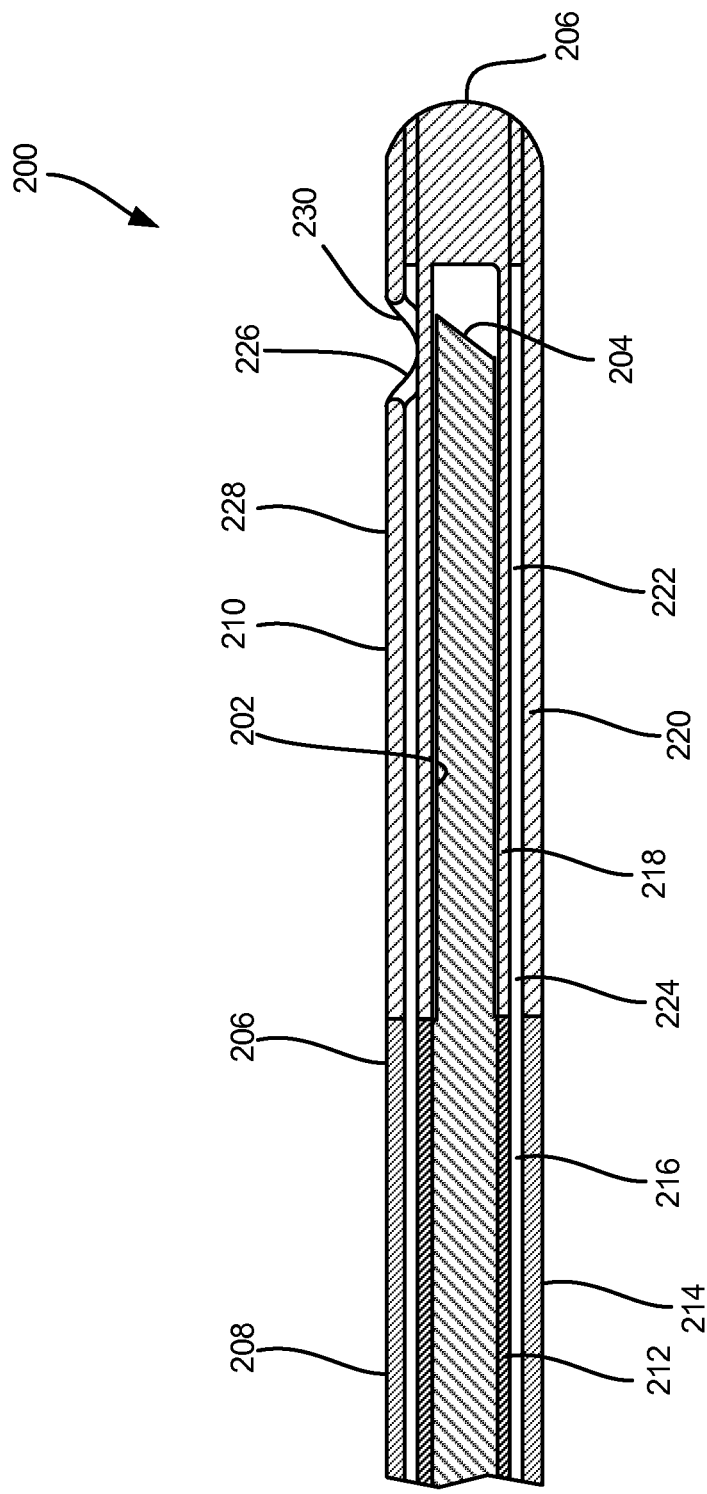
FIG. 3 is a section view of the optical fiber of FIG. 2.

Referring now to FIGS. 2 and 3, optical fiber 200 of the present invention generally comprises an internal fiber 202 defining a fiber tip 204 at a treatment end 205 of the optical fiber 200. Internal fiber 202 is manufactured from a silicon material, typical of optical fibers. Internal fiber 202 is protected from damage prior to use and during introduction to the treatment location with a protective jacket assembly 206. Projective jacket assembly 206 generally comprises a body tube assembly 208 and a tip cap assembly 210. Body tube assembly 208 generally protects a majority portion of the internal fiber 202, extending from proximal end 119 to the tip cap assembly 210. Body tube assembly 208 generally comprises an internal fiber jacket 212, and an external body tube 214 with a body tube channel 216 defined therebetween. Similar to internal fiber 202, internal fiber jacket 212 and external body tube 214 are constructed of a suitable silicon material.

As illustrated in FIG. 3, tip cap assembly 210 generally comprises an inner cap member 218, and an outer cap member 220 defining a cap irrigation channel 222 therebetween. Together, cap irrigation channel 222 and body tube channel 216 cooperatively define an internal irrigation channel 224. Outer cap member 220 includes a side port 226 positioned within an exterior surface 228. Side port 226 generally defines a radiused edge 230, such that laser energy can be directed from the fiber tip 204 to the treatment location.

Figure 4:
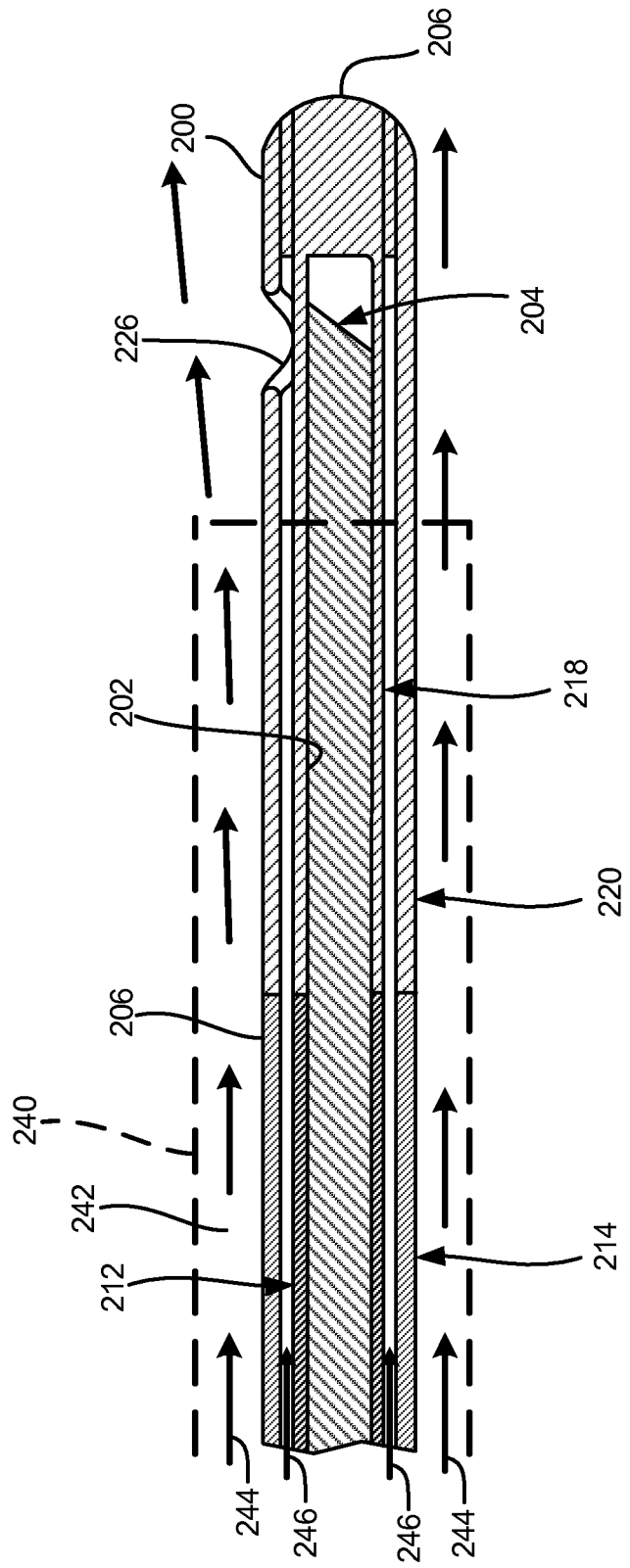
FIG. 4 is a section view of the optical fiber of FIG. 2 being introduced to a treatment location with a cystoscope according to an embodiment of the present invention.

In operation, optical fiber 200 and, more specifically, fiber tip 204, can be introduced to the treatment location utilizing a conventional cystoscope 240, as shown in FIG. 4. Generally, the cystoscope 240 is advanced through the urethra and proximate the treatment area. Once the cystoscope 240 is positioned at the treatment area, an irrigant such as water or saline can be injected through the cystoscope 240. When performing a medical laser procedure with the laser system 100, optical fiber 200 is advanced through the cystoscope 240 such that side port 226 is positioned proximate the desired treatment location.

With the side port 226 oriented toward the treatment location, saline is simultaneously directed through the internal irrigation channel 224, and in an external irrigation channel 242 defined between the cystoscope 240 and the protective jacket assembly 206. With an external cooling stream 244 flowing across exterior surface 228, and an internal cooling stream 246 flowing between the outer cap member 220 and the inner cap member 218, control system 116 directs laser energy through the optical fiber 200 such that a treatment beam exits the fiber tip 204 and out the side port 226. As the treatment beam contacts the treatment location, heat is generated at a tissue surface as the laser energy ablates the targeted tissue. The dual simultaneous cooling of the external cooling stream 244 and the internal cooling stream 246 remove heat energy from the fiber tip 204. As fiber tip 204 is prevented from overheating, ablated tissue is kept from adhering within or around the side port 226, or to the exterior surface 228. In addition, the outer cap member 220 provides a gap between the fiber tip 204 and the treatment location, such that tissue does not attach to the fiber tip 204 due to localized heating at the fiber tip 204. With heat energy removed at the tip cap assembly 210, overheating is avoided such that devitrification and cratering of optical fiber 200 does not occur.

Figure 5:
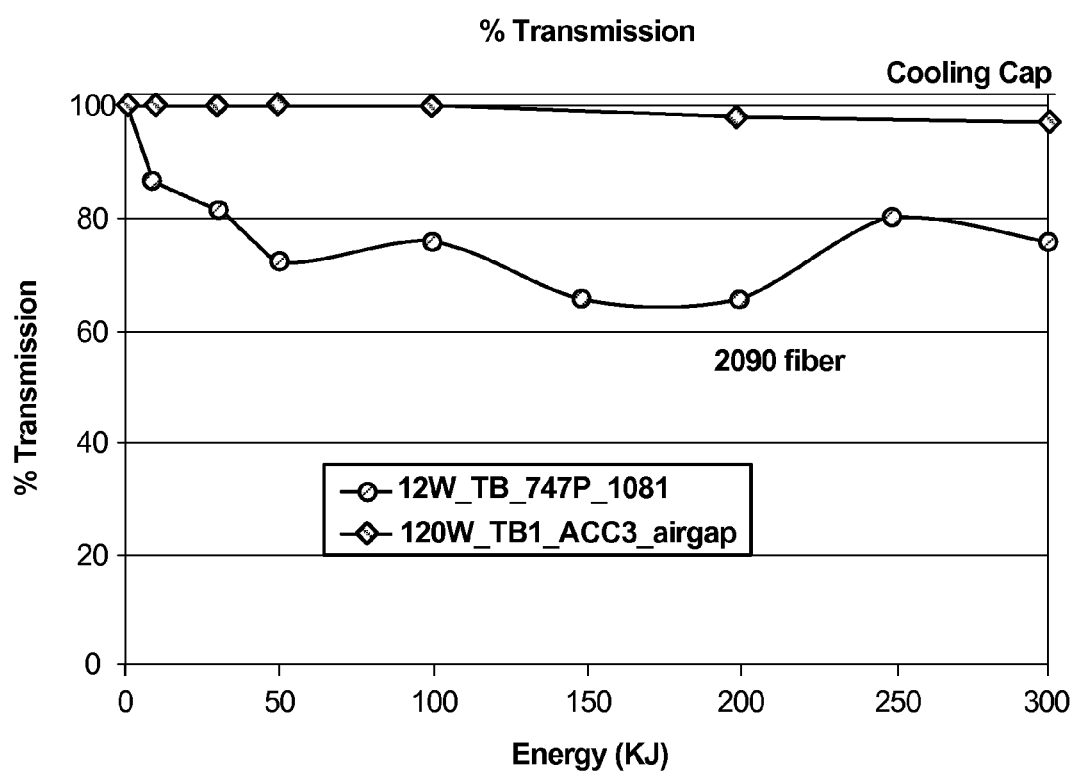
FIG. 5 is a graph comparing percentage of transmission of an optical fiber (2090 fiber) to an optical fiber with the active cooling cap of the present invention.

FIG. 5 provides a comparison between the standard 2090 fiber that is typically used with a GreenLight HPS laser treatment device for treatment of benign prostate hyperplasia (BPH) and the fiber with the active cooling cap of the present invention. As shown, the percentage of transmission of light stays steady in the fiber with the active cooling cap, while the 2090 fiber experiences intermittent decreases in transmission of light as energy is increased. As indicated by the graph, the active cooling cap fiber of the present invention provides reduced laser energy absorption by preventing the tissue contact at the laser firing point and the areas adjacent to the firing point; the tissue is in contact with the outer cap rather than the inner cap through which the laser light is being delivered. Further, the irrigation fluid from the inner cap pushes the tissue debris out of the firing point of the inner cap and, hence, further prevents tissue debris from depositing and burning at the firing point. Moreover, the active cooling cap of the present invention can provide cooling from inside of the cap even when the irrigation fluid from the cystoscope is totally blocked by tissue.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

We claim:

1. An optical fiber comprising:
   an internal fiber terminating at a fiber tip;
   an end surface that reflectively transmits laser energy delivered through the internal fiber;
   a first cap member extending over the end surface;
   a second cap member extending over the first cap member the second cap member being attached to a distal end of the first cap member and having a port through which laser energy is transmitted; and
   a cap irrigation channel between the first cap member and the second cap member.

2. The optical fiber of claim 1, further comprising a body tube assembly surrounding a portion of the internal fiber, the body tube assembly including an internal fiber jacket, an external body tube, and a body tube channel between the internal body tube and the external body tube, wherein the cap irrigation channel and the body tube channel cooperatively define an internal irrigation channel.

3. The optical fiber of claim 2, wherein the body tube assembly, first cap member, second cap member and cap irrigation channel are adapted for introduction through a lumen of a device, whereupon an internal fluid flow can be directed through the internal irrigation channel and an external fluid flow can be directed through an external irrigation channel defined between an interior surface of the lumen, an exterior surface of the body tube assembly, and an exterior surface of the second cap member.

4. The optical fiber of claim 1, wherein laser energy delivered through the internal fiber and transmitted from the end surface is transmitted through the first cap member.

5. The optical fiber of claim 1, wherein the second cap member provides a physical barrier preventing contact between the fiber tip and the treatment location during a treatment procedure.

6. An optical fiber comprising:
   an internal fiber terminating at a fiber tip;
   a reflective surface that reflects laser energy transmitted through the internal fiber;
   an inner cap member extending over the reflective surface;
   an outer cap member extending over the inner cap member, the outer cap member being attached to a distal end of the inner cap member and including an exterior surface having a side-firing port through which laser energy transmitted through the internal fiber and reflected by the reflective surface is discharged; and
   a cap irrigation channel between the inner cap member and the outer cap member.

7. The optical fiber of claim 6, further comprising a body tube assembly surrounding a portion of the internal fiber, the body tube assembly including an internal fiber jacket, an external body tube, and a body tube channel between the internal body tube and the external body tube, wherein the cap irrigation channel and the body tube channel cooperatively define an internal irrigation channel.

8. The optical fiber of claim 7, wherein the body tube assembly, inner cap member, outer cap member and cap irrigation channel are adapted for introduction through a lumen of a device, whereupon an internal fluid flow can be directed through the internal irrigation channel and an external fluid flow can be directed an external irrigation channel defined between an interior surface of the lumen, an exterior surface of the body tube assembly, and an exterior surface of the outer cap member.

9. The optical fiber of claim 6, wherein the outer cap member provides a physical barrier preventing contact between the fiber tip and a treatment location during a treatment procedure.

10. An optical fiber comprising:
    an internal fiber terminating at a fiber tip;
    a reflective surface that reflects laser energy transmitted through the internal fiber; and a tip cap assembly comprising:
- an inner cap member extending over the reflective surface and including a proximal end on a proximal side of the reflective surface and a distal end on a distal side of the reflective surface;
- an outer cap member extending over the inner cap member and including (i) a distal end on the distal side of the reflective surface, the distal end of the outer cap member being attached to the distal end of the inner cap member and (ii) an exterior surface having a port through which laser energy transmitted through the internal fiber and reflected by the reflective surface is discharged; and
- a cap irrigation channel between the inner cap member and the outer cap member.

11. The optical fiber of claim 10, further comprising a body tube assembly surrounding a portion of the internal fiber and including an internal fiber jacket, an external body tube, and a body tube channel between the internal body tube and the external body tube, wherein the cap irrigation channel and the body tube channel cooperatively define an internal irrigation channel.

12. The optical fiber of claim 11, wherein the body tube assembly and the tip cap assembly are adapted for introduction through a lumen of a device, whereupon an internal fluid flow can be directed through the internal irrigation channel and an external fluid flow can be directed through an external irrigation channel defined between an interior surface of the lumen, an exterior surface of the body tube assembly, and an exterior surface of the outer cap member.

13. The optical fiber of claim 10, wherein the outer cap member provides a physical barrier preventing contact between the fiber tip and a treatment location during a treatment procedure.

14. The optical fiber of claim 10, wherein the cap irrigational channel is configured to direct a fluid distally out of the tip cap assembly.

15. The optical fiber of claim 14, wherein the inner and outer cap members extend along a first axis and the port is opposite of the reflective surface along a second axis transverse with the first axis.

16. The optical fiber of claim 15, further comprising a fluid exit port configured to direct the fluid distally along the first axis.

17. The optical fiber of claim 16, wherein the fluid exit port includes an annular opening coaxial with the first axis.

18. A medical laser system comprising:
- a laser unit for generating laser treatment energy; and
- an optical fiber attached to the laser unit for delivering the laser treatment energy to a treatment location, the optical fiber comprising:
  - an internal fiber terminating at a fiber tip and including a reflective surface that reflects laser energy transmitted through the internal fiber; and
  - a tip cap assembly comprising:
    - an inner cap member extending over the reflective surface;
    - an outer cap member extending over the inner cap member and being attached to a distal end of the inner cap member, the outer cap member including an exterior surface having a side-firing port through which laser energy transmitted through the internal fiber and reflected by the reflective surface is discharged; and
    - a cap irrigation channel between the inner cap member and the outer cap member.

19. The medical laser system of claim 18, further comprising:
- a device for accessing a treatment site within a patient's body, the device having a lumen extending therethrough, the optical fiber being adapted for insertion through the lumen such that an external fluid flow can be directed between an interior surface of the lumen and an external surface the optical fiber.

20. The medical laser system of claim 19, wherein the device is a cystoscope.

* * * * *